(12) United States Patent
Pendse (10) Patent No.: US 8,890,656 B2
(45) Date of Patent: Nov. 18, 2014

(54) MOBILE PANIC BUTTON FOR HEALTH MONITORING SYSTEM

(75) Inventor: Ajit Pendse, Durham, NC (US)

(73) Assignee: Pomdevices, LLC, Durham, NC (US)

( * ) Notice: Subject to any disclaimer, the term of this patent is extended or adjusted under 35 U.S.C. 154(b) by 229 days.

(21) Appl. No.: 13/218,378

(22) Filed: Aug. 25, 2011

(65) Prior Publication Data

US 2012/0052833 A1 Mar. 1, 2012

Related U.S. Application Data

(63) Continuation-in-part of application No. 13/151,528, filed on Jun. 2, 2011, now Pat. No. 8,409,013, and a (Continued)

(51) Int. Cl.
| | | |
|---|---|---|
| *G08B 5/22* | (2006.01) | |
| *H04Q 1/30* | (2006.01) | |
| *G06F 19/00* | (2011.01) | |
| *G08B 25/01* | (2006.01) | |
| *G06F 1/16* | (2006.01) | |
| *H04W 4/22* | (2009.01) | |
| *H04M 1/725* | (2006.01) | |
| *H04W 4/12* | (2009.01) | |
| *H04W 88/06* | (2009.01) | |
| *H04L 29/08* | (2006.01) | |
| *H04W 4/00* | (2009.01) | |

(52) U.S. Cl.
CPC ............ *H04W 4/22* (2013.01); *G06F 19/3418* (2013.01); *H04M 2242/04* (2013.01); *H04W 4/12* (2013.01); *G08B 25/016* (2013.01); *H04W 88/06* (2013.01); *G06F 1/1632* (2013.01); *H04L 67/1095* (2013.01); *H04M 1/72541* (2013.01); *H04W 4/008* (2013.01)
USPC .......... 340/7.5; 340/3.1; 340/540; 340/573.1; 455/556.1; 455/404.2

(58) Field of Classification Search
USPC .............. 340/7.5, 3.1, 540, 573.1; 455/404.1, 455/556.1, 404.2
See application file for complete search history.

(56) References Cited

U.S. PATENT DOCUMENTS

| | | | |
|---|---|---|---|
| 4,956,825 | A | 9/1990 | Wilts et al. |
| 5,101,476 | A | 3/1992 | Kukla |

(Continued)

FOREIGN PATENT DOCUMENTS

| | | |
|---|---|---|
| WO | 2011143326 A1 | 11/2011 |
| WO | 2011153373 A1 | 12/2011 |
| WO | 2012/027661 A1 | 3/2012 |

OTHER PUBLICATIONS

United States PCT Office, "International Search Report and Written Opinion of the International Searching Authority" for PCT/US11/36093 filed on May 11, 2011; Aug. 23, 2011.

(Continued)

*Primary Examiner* — Benjamin C Lee
*Assistant Examiner* — Quang D Pham
(74) *Attorney, Agent, or Firm* — Stolowitz Ford Cowger LLP (57) ABSTRACT

In one example, a mobile device with a panic button includes a surface structured to removably engage a surface of a docking station. The mobile device includes a first interface to communicatively couple the mobile device to the docking station at least when the surfaces are engaged, the first interface comprising a short range wireless transceiver or an electrical connector to make contact an electrical connector of the docking station. The mobile device includes a second interface comprising a long range wireless radio. A processing device of the mobile device is configured to relay messages between the docking station and a remote caregiver computing device using the first and second interfaces to enable synchronization between the mobile device and the docking station.

13 Claims, 6 Drawing Sheets

Related U.S. Application Data continuation-in-part of application No. 13/151,034, filed on Jun. 1, 2011, and a continuation-in-part of application No. 13/104,371, filed on May 10, 2011, now Pat. No. 8,427,302, and a continuation-in-part of application No. 13/102,300, filed on May 6, 2011, and a continuation-in-part of application No. 13/151,572, filed on Jun. 2, 2011, and a continuation-in-part of application No. 13/217,649, filed on Aug. 25, 2011.

(60) Provisional application No. 61/378,540, filed on Aug. 31, 2010.

(56) References Cited

U.S. PATENT DOCUMENTS

| | | | | |
|---|---|---|---|---|
| 5,146,562 | A | 9/1992 | Kukla | |
| 5,568,487 | A | 10/1996 | Sitbon et al. | |
| 5,589,818 | A * | 12/1996 | Queen | 340/506 |
| 5,717,379 | A * | 2/1998 | Peters | 340/539.25 |
| 5,967,975 | A | 10/1999 | Ridgeway | |
| 6,078,924 | A | 6/2000 | Ainsbury et al. | |
| 6,138,026 | A * | 10/2000 | Irvin | 455/456.3 |
| 6,216,008 | B1 | 4/2001 | Lee | |
| 6,226,510 | B1 * | 5/2001 | Boling et al. | 455/404.2 |
| 6,247,018 | B1 | 6/2001 | Rheaume | |
| 6,330,499 | B1 * | 12/2001 | Chou et al. | 701/31.4 |
| 6,473,621 | B1 | 10/2002 | Heie | |
| 6,518,889 | B2 * | 2/2003 | Schlager et al. | 340/573.1 |
| 6,807,564 | B1 * | 10/2004 | Zellner et al. | 709/206 |
| 7,111,044 | B2 | 9/2006 | Lee | |
| 7,231,262 | B2 | 6/2007 | Hollis et al. | |
| 7,254,221 | B2 | 8/2007 | Koch | |
| 7,367,888 | B1 | 5/2008 | Chen | |
| 7,409,044 | B2 * | 8/2008 | Leduc | 379/37 |
| 7,486,194 | B2 * | 2/2009 | Stanners et al. | 340/574 |
| 7,586,418 | B2 * | 9/2009 | Cuddihy et al. | 340/573.1 |
| 7,616,110 | B2 * | 11/2009 | Crump et al. | 340/539.11 |
| 7,928,851 | B2 * | 4/2011 | Stanners et al. | 340/574 |
| 7,937,066 | B2 * | 5/2011 | Kaltsukis | 455/404.1 |
| 8,249,547 | B1 * | 8/2012 | Fellner | 455/404.1 |
| 8,359,000 | B2 * | 1/2013 | Fee | 455/404.2 |
| 8,409,013 | B2 | 4/2013 | Pendse | |
| 8,427,302 | B2 | 4/2013 | Pendse | |
| 8,472,915 | B2 * | 6/2013 | DiPerna et al. | 455/404.1 |
| 8,510,394 | B2 * | 8/2013 | Zellner et al. | 709/206 |
| 2001/0044337 | A1 | 11/2001 | Rowe | |
| 2001/0049609 | A1 | 12/2001 | Girouard | |
| 2002/0019747 | A1 | 2/2002 | Ware et al. | |
| 2002/0080033 | A1 * | 6/2002 | Shepher | 340/573.1 |
| 2003/0114106 | A1 * | 6/2003 | Miyatsu et al. | 455/41 |
| 2003/0119561 | A1 | 6/2003 | Hatch | |
| 2004/0067475 | A1 | 4/2004 | Niddrie | |
| 2004/0073460 | A1 | 4/2004 | Erwin | |
| 2004/0128163 | A1 | 7/2004 | Goodman et al. | |
| 2004/0203961 | A1 | 10/2004 | Rustici et al. | |
| 2004/0209604 | A1 | 10/2004 | Urban | |
| 2004/0247748 | A1 | 12/2004 | Bronkema | |
| 2005/0033124 | A1 * | 2/2005 | Kelly et al. | 600/300 |
| 2005/0086082 | A1 | 4/2005 | Braunstein | |
| 2005/0132069 | A1 | 6/2005 | Shannon et al. | |
| 2005/0136953 | A1 | 6/2005 | Jo | |
| 2005/0136954 | A1 | 6/2005 | Itoh | |
| 2005/0149359 | A1 | 7/2005 | Steinberg | |
| 2005/0151640 | A1 * | 7/2005 | Hastings | 340/539.11 |
| 2005/0215844 | A1 | 9/2005 | Ten Eyck | |
| 2005/0222933 | A1 | 10/2005 | Wesby | |
| 2006/0031094 | A1 | 2/2006 | Cohen | |
| 2006/0058048 | A1 | 3/2006 | Kapoor | |
| 2006/0066448 | A1 | 3/2006 | Berisford et al. | |
| 2006/0089542 | A1 * | 4/2006 | Sands | 600/300 |
| 2006/0195586 | A1 * | 8/2006 | Stoyanov et al. | 709/227 |
| 2006/0281543 | A1 | 12/2006 | Sutton | |
| 2006/0287068 | A1 | 12/2006 | Walker | |
| 2007/0066403 | A1 | 3/2007 | Conkwright | |
| 2007/0192738 | A1 | 8/2007 | Lee | |
| 2007/0200927 | A1 | 8/2007 | Krenik | |
| 2007/0281720 | A1 * | 12/2007 | Lee | 455/466 |
| 2008/0009300 | A1 | 1/2008 | Vuong | |
| 2008/0027337 | A1 | 1/2008 | Dugan et al. | |
| 2008/0108386 | A1 * | 5/2008 | Hard | 455/557 |
| 2008/0131851 | A1 * | 6/2008 | Kanevsky et al. | 434/157 |
| 2008/0218376 | A1 | 9/2008 | Dicks et al. | |
| 2008/0243544 | A1 | 10/2008 | Cafer | |
| 2008/0285592 | A1 * | 11/2008 | Emmendorfer et al. | 370/474 |
| 2009/0098925 | A1 | 4/2009 | Gagner | |
| 2009/0105550 | A1 | 4/2009 | Rothman et al. | |
| 2009/0319298 | A1 | 12/2009 | Weiss et al. | |
| 2010/0023348 | A1 | 1/2010 | Hardee et al. | |
| 2010/0036991 | A1 * | 2/2010 | Lee | 710/304 |
| 2010/0153881 | A1 | 6/2010 | Dinn | |
| 2010/0217807 | A1 * | 8/2010 | Hawkins | 709/206 |
| 2010/0311387 | A1 * | 12/2010 | Cameron et al. | 455/404.2 |
| 2011/0021247 | A1 * | 1/2011 | Shih | 455/557 |
| 2011/0053643 | A1 * | 3/2011 | Shmunis | 455/556.1 |
| 2011/0054292 | A1 * | 3/2011 | Hirson et al. | 600/407 |
| 2011/0103342 | A1 * | 5/2011 | Cho et al. | 370/329 |
| 2011/0107437 | A1 * | 5/2011 | Goyal et al. | 726/30 |
| 2011/0281597 | A1 | 11/2011 | Pendse | |
| 2011/0285529 | A1 | 11/2011 | Pendse | |
| 2011/0300945 | A1 | 12/2011 | Pendse | |
| 2011/0301969 | A1 | 12/2011 | Pendse | |
| 2012/0050066 | A1 | 3/2012 | Pendse | |
| 2012/0064855 | A1 * | 3/2012 | Mendelson | 455/404.2 |
| 2013/0017846 | A1 | 1/2013 | Schoppe | |
| 2013/0176128 | A1 | 7/2013 | Pendse | |
| 2013/0190905 | A1 | 7/2013 | Pendse | |

OTHER PUBLICATIONS

United States PCT Office, "International Search Report and Written Opinion of the International Searching Authority" for PCT/US11/38960 filed on Jun. 2, 2011; Aug. 26, 2011.
United States PCT Office, "International Search Report and Written Opinion of the International Searching Authority" for PCT/US11/49332 filed on Aug. 26, 2011; Dec. 19, 2011.
Stolowitz Ford Cowger, Listing of Related Cases, Dec. 28, 2011.
U.S. Appl. No. 13/151,034, filed May 10, 2011.
U.S. Appl. No. 13/217,649, filed Aug. 25, 2011.
"The Aware Home: A Living Laboratory for Ubiquitous Computing Research" Cory D. Kidd, Robert J. Orr, Gregory D. Abowd, Christopher G. Atkeson, Irfan A. Essa, Blair MacIntyre, Elizabeth Mynatt, Thad E. Starner and Wendy Newstetter. In the Proceedings of the Second International Workshop on Cooperative Buildings—CoBuild'99. Position paper; Oct. 1999; This paper explains some of our vision on technology—and human—centered research themes; 3 pages.

* cited by examiner

MOBILE PANIC BUTTON FOR HEALTH MONITORING SYSTEM

This application is a non-provisional of U.S. Provisional Application No. 61/378,540 filed on Aug. 31, 2010, entitled: MOBILE PANIC BUTTON FOR HEALTH MONITORING SYSTEM, and a continuation in part of U.S. Non-provisional application Ser. No. 13/151,528 filed on Jun. 2, 2011, entitled: INTERACTIVE ELECTRONIC GAME RESULTS AS HEALTH INDICATORS, and a continuation in part of U.S. Non-provisional application Ser. No. 13/151,034 filed on Jun. 1, 2011, entitled: META SMS/TEXT DATA EXTRACTION, and a continuation in part of U.S. Non-provisional application Ser. No. 13/104,371 filed on May 10, 2011, entitled: ACTIVITY TREND DETECTION AND NOTIFICATION TO A CAREGIVER, and a continuation in part of U.S. Non-provisional application Ser. No. 13/102,300 filed on May 6, 2011, entitled: AIDED CONSTRUCTION OF SMS STATUS MESSAGES TO CAREGIVERS, and a continuation in part of U.S. Non-provisional Application No. 13/151,572 filed on Jun. 2, 2011, entitled: MONITORING ELECTRONIC DEVICE USAGE IN A MANAGED HEALTHCARE ENVIRONMENT, and a continuation in part of U.S. Non-provisional application Ser. No. 13/217,649 filed on Aug. 25, 2011, entitled: MOBILE DEVICE USER INTERFACE FOR HEALTH MONITORING SYSTEM, each of which is incorporated herein by reference in its entirety.

COPYRIGHT NOTICE

©2010-2011 pomdevices, LLC. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

BACKGROUND OF THE INVENTION

Many devices and services have been provided to consumers that aim to decrease complexity and increase safety and security for the older adult. Such devices are often single-purpose, push button devices that may be worn, carried, or otherwise situated hopefully within reach of an older adult who may need assistance. Such devices transmit basic information such as a device identifier to a central monitoring station or terminal, which then passes the information on to a caregiver or appropriate authorities such as police, fire, medical, or 911 call takers. In life-or-death situations, such a "middle man" can cost the user precious time that could make the difference between life and death.

SUMMARY OF THE INVENTION

In one example, a mobile device including a panic button is provided. The mobile device includes a long range wireless interface (such as radios used in cellular telephones). The mobile device is configured to wirelessly transmit an alert using the long range wireless interface responsive to actuation of the panic button.

An intelligent docking station having a surface structured to engage with the mobile device is also provided. The intelligent docking station includes a wired or short range wireless interface configured to communicatively couple the docking station to the mobile device at least when the surfaces are engaged.

The intelligent docking station includes a processing device configured to connect to a remote caregiver computing device using the long range wireless interface of the mobile device, responsive to the surfaces being engaged (in the case of a wired connection), or responsive to the mobile device coming in range (in the case of a short range wireless connection). The processing device is configured to send or receive information to or from the remote caregiver computing device related to monitoring the health of the mobile device user.

The processing device may also be configured to synchronize the mobile device with some or all of the information sent to or from the remote caregiver computing device during the message exchange. In one example, the information synchronized to the mobile device can include a value for a target address setting of the mobile device. The target address setting controls which remote caregiver device(s) the mobile device notifies responsive to actuation of the panic button. For example, the target address may specify an SMS-capable wireless device telephone number, a land-line telephone number, an email address, etc.

DETAILED DESCRIPTION OF PREFERRED EMBODIMENTS

In one aspect, the present disclosure is directed to provide users with a simple and easy way of contacting both caregivers and governmental authorities or other emergency responders with, for example, a push of a button. In a preferred embodiment, my system would include a docking station, which may be a PC or a custom hardware device. For example, a docking station for this purpose may be a compute station of the type described above, with greater or lesser interfaces and capabilities as appropriate or desired.

The docking station gathers information and provides analysis on the most recent data available for the patient, including medication monitoring, movement through the household, healthcare information, and other variables further described herein. A simple handheld device (clamshell style or otherwise) docks into the intelligent docking station and is made aware of the most recent data, including for example appropriate contacts (agencies, caregivers, emergency call takers, etc), health trends, etc. The handheld device in a presently preferred embodiment may have the following features:

- Mobile communication enabled;
- A central processing unit;
- GPS functionality or other location capability;
- A single, preferably protected (from unintended use), "panic" button;
- Logic card;
- Software for interpreting data from the docking station and optimizing panic output data; and/or
- A hoop, clip, pin, button, etc. for securing the mobile device to a mobile device user or an article of clothing.

In one example, a handheld device having the above components may be significantly smaller than the typical cellular telephone. With regard to user input/output interfaces, the handheld device may have less extensive user input/output interfaces than the docking station. For example, the docking station may have a screen display, whereas the handheld device may have a more limited visual user output interface such as an indicator light, or even no light driven visual output.

The following scenario is illustrative:

Jane had been using a stationary healthcare monitoring device for several months. One morning, Jane forgets to take her medication (which is noted by the docking station) and goes out to pick up groceries. On her way out, Jane picks up her handheld device, which has all of her latest information, including that she forgot (or declined) to take her morning medication.

At the grocery store, Jane falls ill and presses the panic button on her handheld device. The device, using its mobile network connection, sends a message (e.g., pre-recorded voice, real-time voice, SMS text, etc) to both the primary caregiver (e.g. Jane's daughter), and the doctor that had been loaded into Jane's stationary device at home. The message may include most recent health updates, such as the failure to take medication that morning. Jane is rescued in time, which may not have been possible using present solutions.

Figure 1:
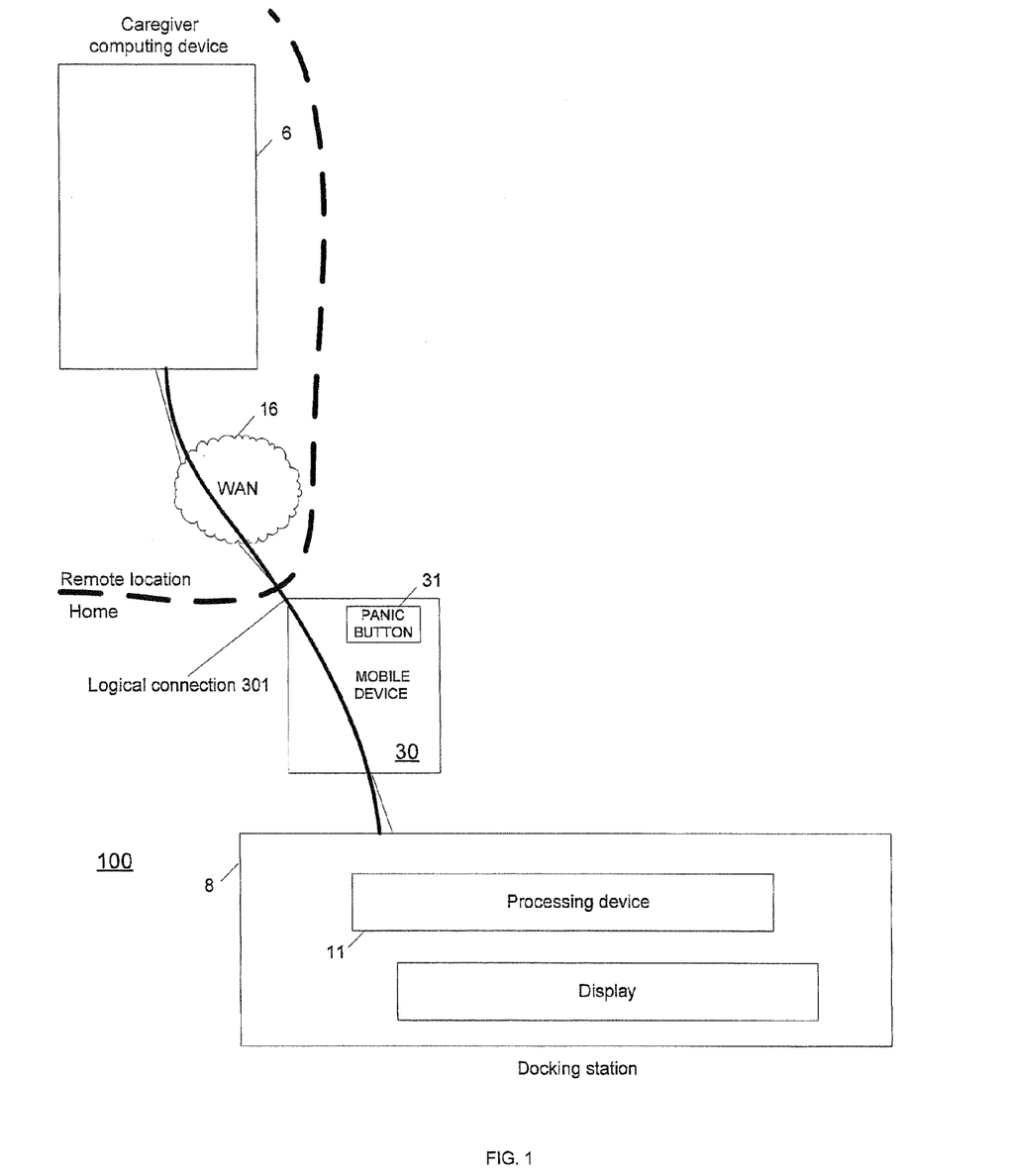
FIG. 1 illustrates a docking station communicating with a remote caregiver computing device through a mobile device.

FIG. 1 illustrates a docking station 8 communicating with the caregiver computing device 6 through a mobile device 30 having a panic button 31. The processing device 11 of the docking station 8 is configured to detect a physical coupling (via a dock or other wired connection such as USB) or a short range wireless coupling (for example Bluetooth) of the mobile device 30 to the docking station 8. The processing device 11 may be configured to establish the logical connection 301 over the Wide Area Network (WAN) 16 responsive to the detection. By the term "WAN" we mean to include any network that covers a broad area, including but not limited to, cellular networks; satellite-based networks; the Publicly Switched Telephone Network (PSTN) and other circuit switched networks; packet switched networks, etc. The logical connection 301 is established through the mobile device 30 using the connection between the mobile device 30 and the portable patient computing device 8, as well as another connection extending from the mobile device 30 (which may be, for example, data service connection to a cell tower).

Having established the logical connection 301, the processing device 11 synchronizes with the remote computing device 6 via the logical connection 301. Synchronization can include sending information to the remote computing device 6, or receiving information from the remote computing device 6. The transmitted information can include medication monitoring information, information on movement of the mobile device user through the home, healthcare information, or any of the information handled by the portable patient computing device described in co-pending U.S. patent application Ser. Nos. 13/151,528, 13/151,034, 13/104,371, 13/102,300, 13/151,572, and 13/217,649, each of which are herein incorporated by reference in their entirety.

Before, after, or in parallel with the remote caregiver computing device synchronization, the processing device 11 synchronizes with the mobile device. This mobile device synchronization can include sending information to the mobile device 30. Such transmitted information can include any portion of the information exchanged during the remote caregiver computing device synchronization, i.e. all or only selected portions of the information exchanged during the remote caregiver computing device synchronization.

In one example, during the mobile device synchronization, the processing device 11 updates a target address setting of the mobile device by, for example, transmitting a value indicating an address of a destination device(s). The target address setting controls which remote device(s) the mobile device notifies responsive to actuation of the panic button.

In another example, during the mobile device synchronization, the processing device 11 transmits information gleaned from patient monitoring, such as data indicating that the mobile device user skipped a dosage of medication. Such transmitted information can be stored on the mobile device 30 for later use, including but not limited to insertion in an emergency message transmitted by the mobile device 30 responsive to actuation of the panic button 31 and/or passive storage on the mobile device 30 to be extracted from the memory device 30 by emergency personnel (or any other caregiver).

Figure 2:
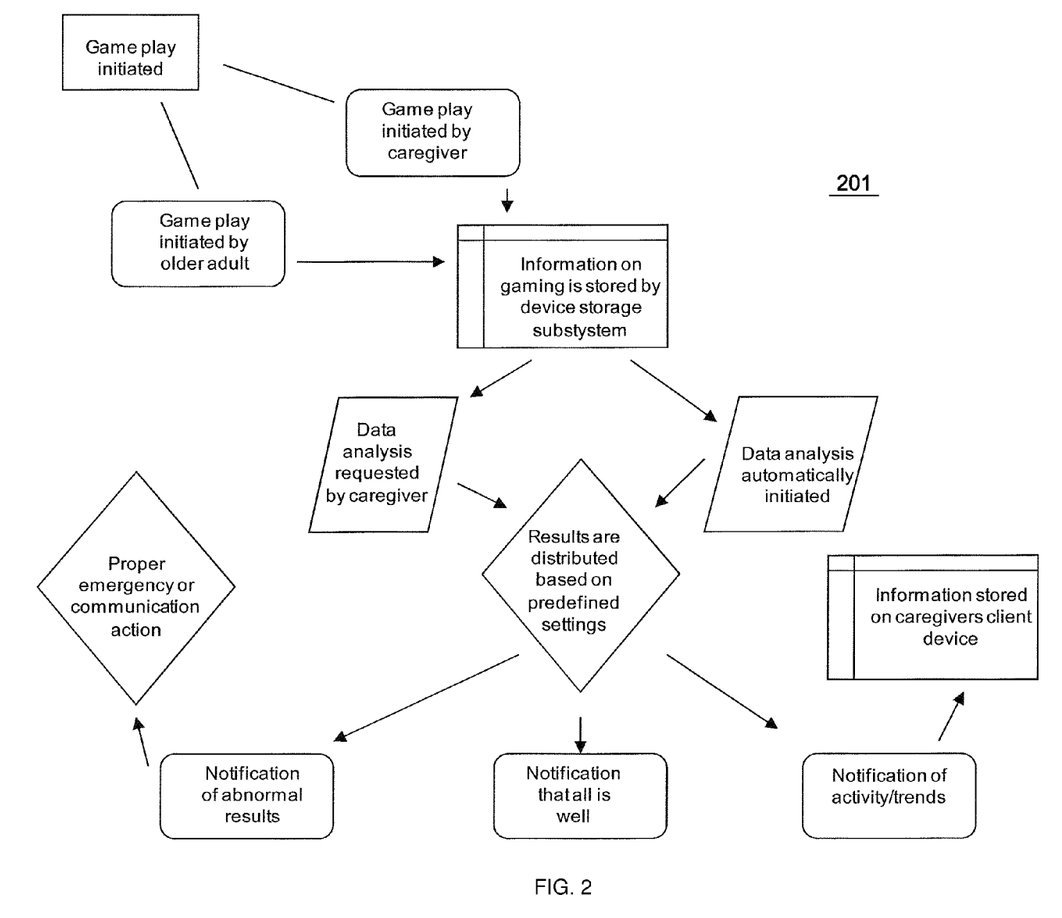
FIG. 2 illustrates a process of using interactive electronic game results as health indicators that may be performed by the docking station of FIG. 1.

FIG. 2 illustrates a process that may be performed by the docking station of FIG. 1. Briefly, this process pertains to capturing data in response to a patient activity, such as playing an electronic game, and analyzing that data to infer changes in the patient's condition.

The processor 11 of docking station 8 may be configured to, alone or in combination with processing performed by a processor of caregiver computing device 6, perform the process 201 shown in FIG. 2, which is described in more detail in U.S. patent application Ser. No. 13/151,528 filed on Jun. 2, 2011 entitled "INTERACTIVE ELECTRONIC GAME RESULTS AS HEALTH INDICATORS", which is herein incorporated by reference in its entirety. Any of the information gathered, transmitted, or stored according to process 201 may be synchronized to the mobile device 30 of FIG. 1, in one example. Any of the information gathered, transmitted, or stored according to process 201, or data derived therefrom thereof (such as a code representative of the information), may be inserted by the mobile device 30 into an emergency response message responsive to actuation of the panic button.

Figure 3:
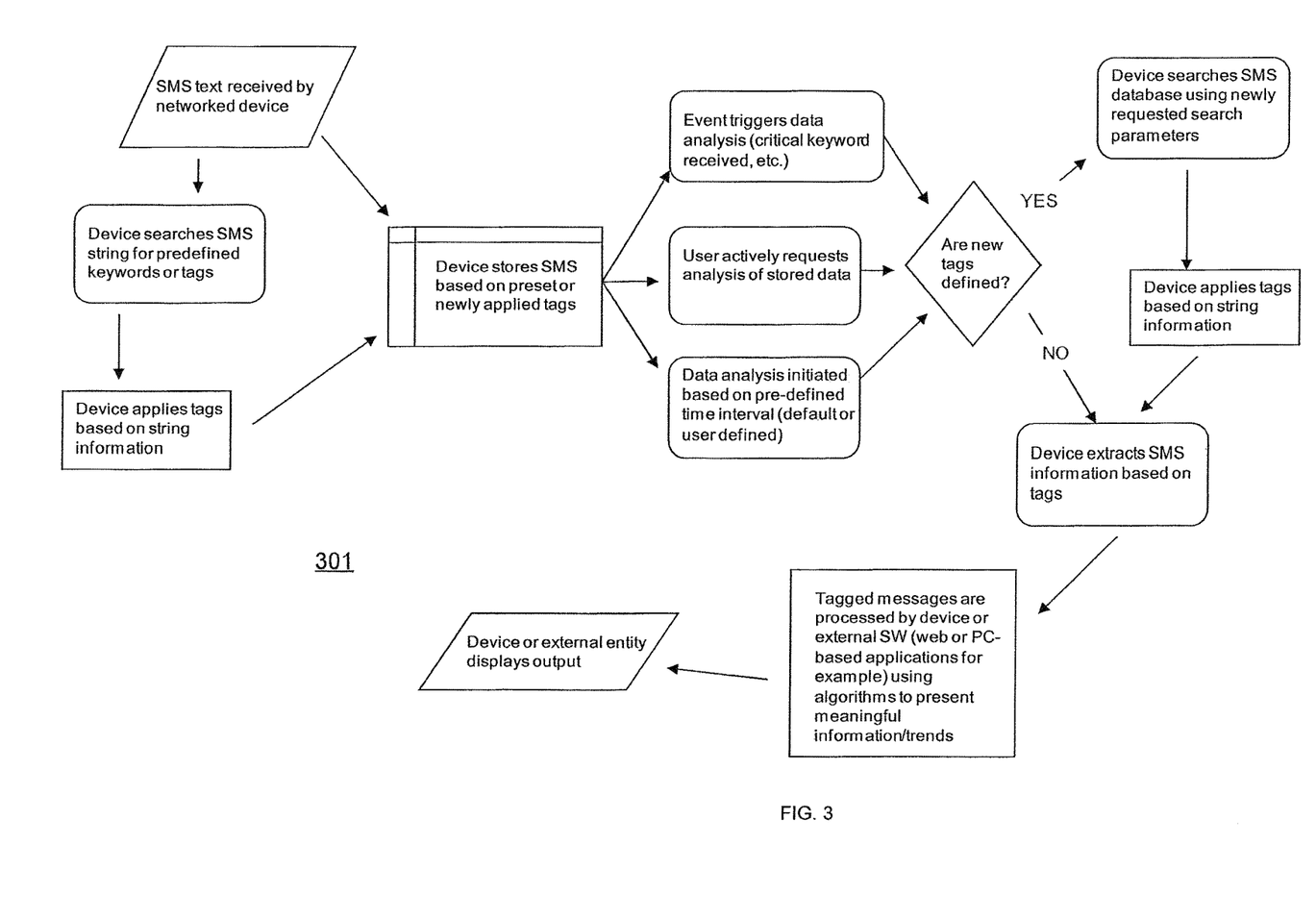
FIG. 3 illustrates a process of tagging text messages for health monitoring that may be performed by the docking station of FIG. 1.

FIG. 3 illustrates another process that may be performed by the docking station of FIG. 1. Briefly, this process pertains to extracting and analyzing data contained in multiple SMS or "text messages" received by a processor such as a remote caregiver device.

The processor 11 of docking station 8 may be configured to, alone or in combination with processing performed by a processor of caregiver computing device 6, perform the process 301 shown in FIG. 3, which is described in more detail in U.S. patent application Ser. No. 13/151,034 filed on Jun. 1, 2011 entitled "META SMS/TEXT DATA EXTRACTION", which is herein incorporated by reference in its entirety. Any of the information gathered, transmitted, or stored according to process 301 may be synchronized to the mobile device 30 of FIG. 1, in one example. Any of the information gathered, transmitted, or stored according to process 301, or data derived therefrom (such as a code representative of the information), may be inserted by the mobile device 30 into an emergency response message responsive to actuation of the panic button.

Figure 4:
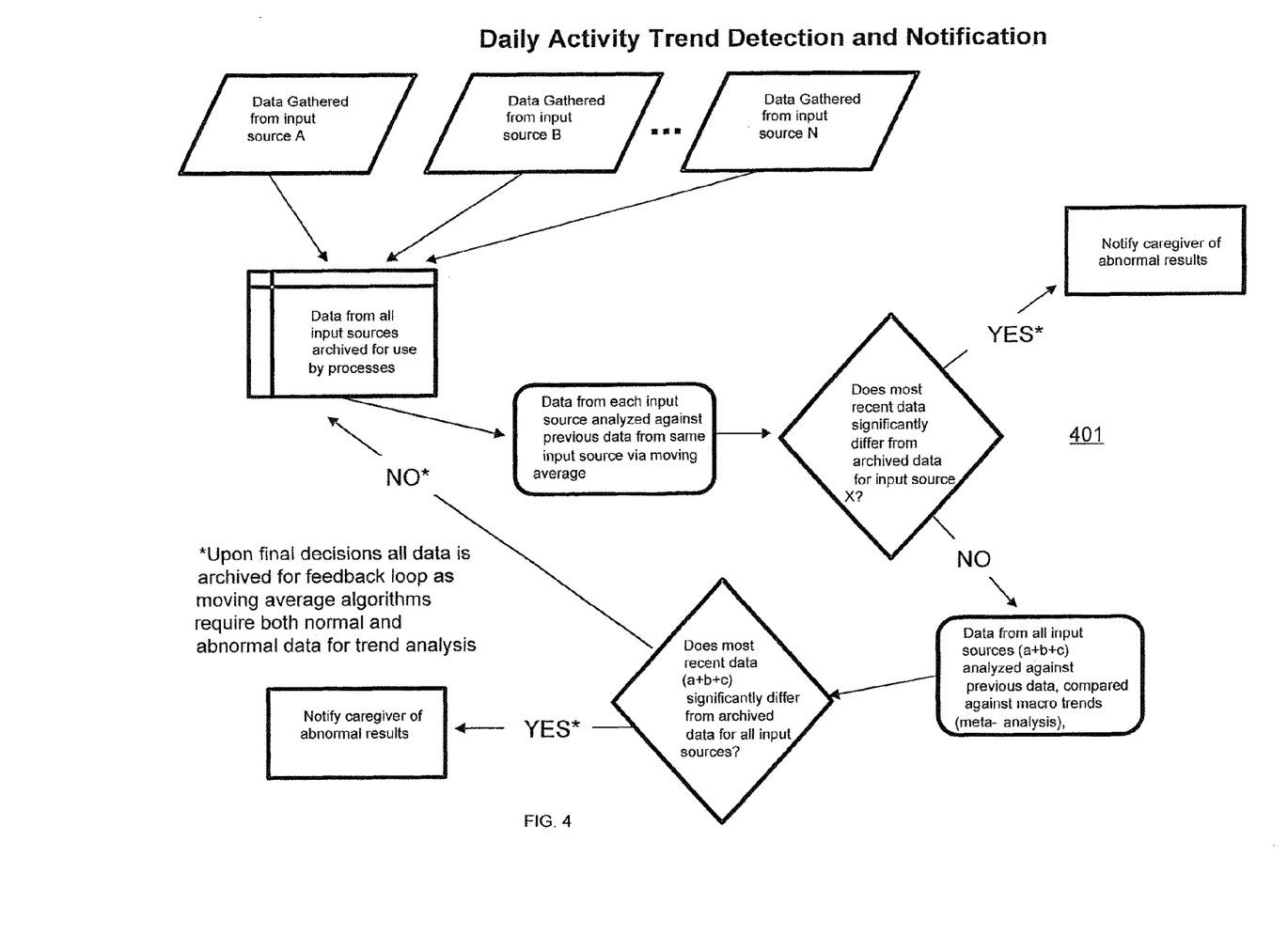
FIG. 4 illustrates a process of activity trend detection for health monitoring that may be performed by the docking station of FIG. 1.

FIG. 4 illustrates another process that may be performed by the docking station of FIG. 1. Briefly, this process relates to trend analysis of a patient's daily activity and notifications to caregivers as may be indicated.

The processor 11 of docking station 8 may be configured to, alone or in combination with processing performed by a processor of caregiver computing device 6, perform the process 401 shown in FIG. 4, which is described in more detail in U.S. patent application Ser. No. 13/104,371 filed on May 10, 2011 entitled "ACTIVITY TREND DETECTION AND NOTIFICATION TO A CAREGIVER", which is herein incorporated by reference in its entirety. Any of the information gathered, transmitted, or stored according to process 401 may be synchronized to the mobile device 30 of FIG. 4, in one example. Any of the information gathered, transmitted, or stored according to process 401, or data derived therefrom thereof (such as a code representative of the information), may be inserted by the mobile device 30 into an emergency response message responsive to actuation of the panic button.

Figure 5:
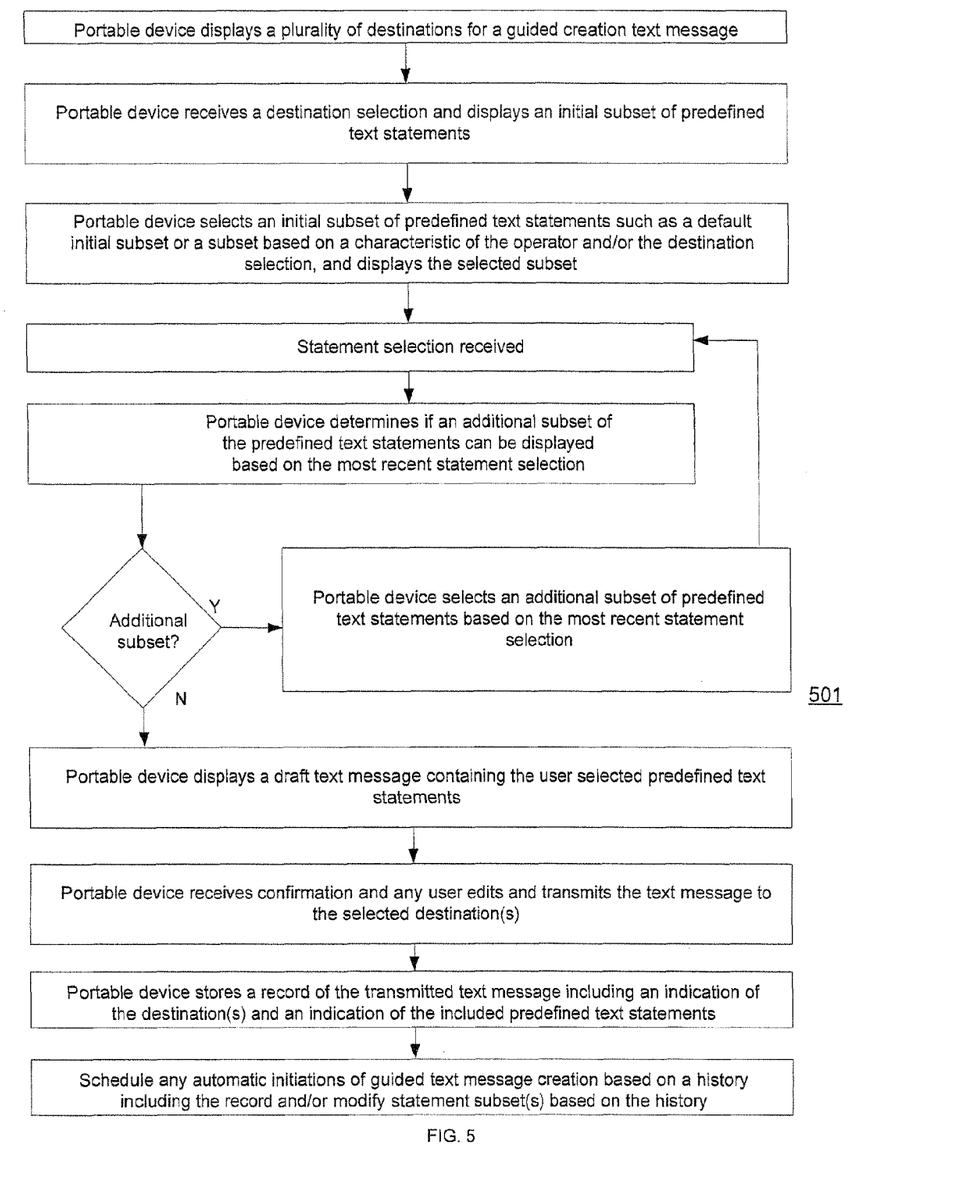
FIG. 5 illustrates a process of aided construction of SMS messages to caregivers that may be performed by the docking station of FIG. 1.

FIG. 5 illustrates another process that may be performed by the docking station of FIG. 1. Briefly, this process pertains to aided construction of SMS status messages to caregivers.

The processor 11 of docking station 8 may be configured to, alone or in combination with processing performed by a processor of caregiver computing device 6, perform the process 501 shown in FIG. 5, which is described in more detail in U.S. patent application Ser. No. 13/102,300 filed on May 6, 2011 entitled "AIDED CONSTRUCTION OF SMS STATUS MESSAGES TO CAREGIVERS", which is herein incorporated by reference in its entirety. Any of the information gathered, transmitted, or stored according to process 501 may be synchronized to the mobile device 30 of FIG. 5, in one example. Any of the information gathered, transmitted, or stored according to process 501, or data derived therefrom thereof (such as a code representative of the information), may be inserted by the mobile device 30 into an emergency response message responsive to actuation of the panic button.

Figure 6:
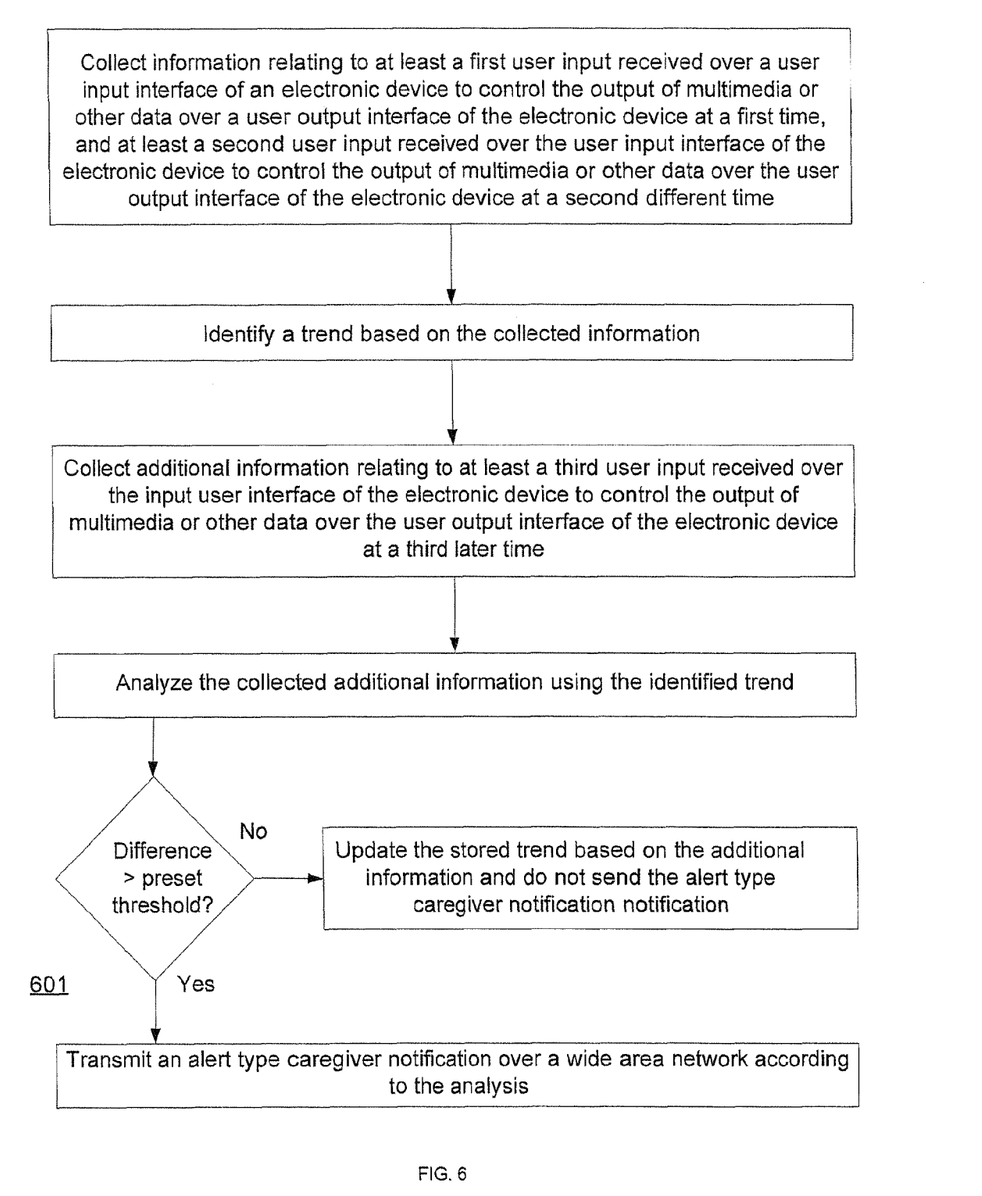
FIG. 6 illustrates a process of collecting electronic device usage information for health monitoring that may be performed by the docking station of FIG. 1.

FIG. 6 illustrates another process that may be performed by the docking station of FIG. 1. Briefly, this process pertains to collecting information from electronic devices, such as multimedia capable entertainment devices, for detecting a change in health of a patient.

The processor 11 of docking station 8 may be configured to, alone or in combination with processing performed by a processor of caregiver computing device 6, perform the process 601 shown in FIG. 6, which is described in more detail in U.S. patent application Ser. No. 13/151,572 filed on Jun. 2, 2011 entitled "MONITORING ELECTRONIC DEVICE USAGE IN A MANAGED HEALTHCARE ENVIRONMENT", which is herein incorporated by reference in its entirety. Any of the information gathered, transmitted, or stored according to process 601 may be synchronized to the mobile device 30 of FIG. 1, in one example. Any of the information gathered, transmitted, or stored according to process 601, or data derived therefrom thereof (such as a code representative of the information), may be inserted by the mobile device 30 into an emergency response message responsive to actuation of the panic button.

Most of the equipment discussed above comprises hardware and associated software. For example, the typical portable device is likely to include one or more processors and software executable on those processors to carry out the operations described. We use the term software herein in its commonly understood sense to refer to programs or routines (subroutines, objects, plug-ins, etc.), as well as data, usable by a machine or processor. As is well known, computer programs generally comprise instructions that are stored in machine-readable or computer-readable storage media. Some embodiments of the present invention may include executable programs or instructions that are stored in machine-readable or computer-readable storage media, such as a digital memory. We do not imply that a "computer" in the conventional sense is required in any particular embodiment. For example, various processors, embedded or otherwise, may be used in equipment such as the components described herein.

Memory for storing software again is well known. In some embodiments, memory associated with a given processor may be stored in the same physical device as the processor ("on-board" memory); for example, RAM or FLASH memory disposed within an integrated circuit microprocessor or the like. In other examples, the memory comprises an independent device, such as an external disk drive, storage array, or portable FLASH key fob. In such cases, the memory becomes "associated" with the digital processor when the two are operatively coupled together, or in communication with each other, for example by an I/O port, network connection, etc. such that the processor can read a file stored on the memory. Associated memory may be "read only" by design (ROM) or by virtue of permission settings, or not. Other examples include but are not limited to WORM, EPROM, EEPROM, FLASH, etc. Those technologies often are implemented in solid state semiconductor devices. Other memories may comprise moving parts, such as a conventional rotating disk drive. All such memories are "machine readable" or "computer-readable" and may be used to store executable instructions for implementing the functions described herein.

A "software product" refers to a memory device in which a series of executable instructions are stored in a machine-readable form so that a suitable machine or processor, with appropriate access to the software product, can execute the instructions to carry out a process implemented by the instructions. Software products are sometimes used to distribute software. Any type of machine-readable memory, including without limitation those summarized above, may be used to make a software product. That said, it is also known that software can be distributed via electronic transmission ("download"), in which case there typically will be a corresponding software product at the transmitting end of the transmission, or the receiving end, or both.

Having described and illustrated the principles of the invention in a preferred embodiment thereof, it should be apparent that the invention may be modified in arrangement and detail without departing from such principles. We claim all modifications and variations coming within the spirit and scope of the following claims.

The invention claimed is:

1. A system, comprising:
a mobile device associated with a patient and including a panic button for operation by the patient, the mobile device configured to wirelessly transmit an emergency message to at least one destination device responsive to actuation of the panic button;
a docking station having a surface structured to removably engage a surface of the mobile device;
a wired or short range wireless first interface on the docking station, the first interface configured to communicatively couple the docking station to the mobile device;
a long range wireless second interface on the mobile device, the second interface configured to communicatively couple the mobile device to a remote network; and a processing device operating within the docking station, the processing device configured to establish a logical connection with a remote caregiver computing device via the remote network using the first interface and the second interface of the mobile device in response to the mobile device communicatively coupling to the docking station;

wherein the processing device is configured to synchronize with the caregiver computing device and the mobile device, the synchronization with the caregiver computing device using the logical connection and including at least one of sending or receiving first information related to the patient, the synchronization with the mobile device including sending second information to the mobile device, wherein the second information is based on the first information, wherein the second information includes data to be inserted into the emergency message or data to be utilized by the mobile device to transmit the emergency message.

2. The system of claim 1, wherein the second information includes a target address setting of the mobile device that is taken from a value included in the first information, the target address setting controlling a destination of the emergency message.

3. The system of claim 1, wherein the processing device is further configured to:
receive a plurality of first communications, each first communication including data indicative of activity of a patient using the mobile device that was captured at a corresponding first time;
receive a plurality of second communications, each second communication including data indicative of activity of the patient using a local or remote device that was captured at a corresponding second time;
identify a trend based on information from the collected first and second communications; and
analyze data received in a new communication from at least one of the mobile device and the local or remote device based on the identified trend;
wherein the at least one of the first information or the second information is based on a result of the analysis.

4. The system of claim 1, wherein the panic button comprises a push button.

5. The system of claim 1, wherein the docking station includes an integrated display screen display and the mobile device does not include an integrated display screen.

6. A mobile device, comprising:
a panic button;
a processing device coupled to the panic button, the processing device configured to wirelessly transmit an emergency message for a patient associated with the mobile device to at least one destination device responsive to actuation of the panic button;
a surface encasing the processing device, at least a portion of the surface structured to removably engage a surface of a docking station;
a first interface coupled to the processing device and configured to communicatively couple the mobile device to the docking station, the first interface comprising a short range wireless transceiver or an electrical connector to make contact with an electrical connector of the docking station;
a long range wireless second interface coupled to the processing device and configured to communicatively couple the mobile device to a remote network;
the processing device further configured to relay first information related to the patient between the docking station and a remote caregiver computing device using the first and second interfaces over a logical connection extending from or to the remote caregiver communication device to or from the docking station via the remote network, wherein the logical connection is established in response to the mobile device communicatively coupling to the docking station; and
the processing device further configured to receive second information from the docking station, wherein the second information is based on the first information, and wherein the second information includes data to be inserted into the emergency message or data to be utilized by the processing device to transmit the emergency message.

7. The mobile device of claim 6, wherein the processing device is further configured to:
update a local target address setting according to a value taken from the second information;
wherein the local target address setting controls a destination of the emergency message.

8. The mobile device of claim 7, wherein the second information comprises a result of a trend analysis by the docking station.

9. The mobile device of claim 6, wherein the surface has integrated thereon a means for attaching the mobile device to the mobile device user or to an article of clothing.

10. The mobile device of claim 9, wherein the attaching means comprises a hoop or a clip.

11. An apparatus, comprising:
a processing device; and
a memory storing instructions that, when executed by the processing device, cause the processing device to:
establish a first connection to a mobile device responsive to the mobile device communicatively coupling to the processing device;
wherein the mobile device is associated with a patient and includes a panic button for operation by the patient, the mobile device to wirelessly transmit an emergency message to at least one destination device responsive to actuation of the panic button;
responsive to establishing the first connection, establish a second connection with a remote caregiver computing device through the mobile device using a long range wireless transmitter of the mobile device, wherein the second connection comprises a logical connection extending between the processing device and the remote caregiver computing device;
response to establishing the second connection using the long range wireless transmitter of the mobile device, synchronize with the remote caregiver computing device over said second connection, the synchronization with the remote caregiver computing device including at least one of sending or receiving first information related to the patient; and
synchronize with the mobile device including sending second information to the mobile device, wherein the second information is based on the first information, wherein the second information includes data to be inserted into the emergency message or data to be utilized by the mobile device to transmit the emergency message.

12. The apparatus of claim 11, further comprising a more extensive user output interface than the mobile device.

13. The apparatus of claim 11, wherein the panic button comprises a push button.

* * * * *